United States Patent [19]

Kimura et al.

[11] 3,951,984
[45] Apr. 20, 1976

[54] 3-BENZAZOCINE COMPOUNDS

[75] Inventors: Michio Kimura; Takeshi Nakajima, both of Minoo; Toshio Atsumi, Ashiya; Kenji Kobayashi; Yoshiaki Takebayashi, both of Takarazuka; Shigeho Inaba, Takarazuka; Hisao Yamamoto, Nishinomiya, all of Japan

[73] Assignee: Sumitomo Chemical Company, Limited, Japan

[22] Filed: Dec. 18, 1973

[21] Appl. No.: 425,717

[52] U.S. Cl. .................. 260/283 R; 260/DIG. 13; 424/258
[51] Int. Cl.² ........................................ C07D 221/26
[58] Field of Search ............... 260/293.54, DIG. 13, 260/293.53, 283 R

[56] References Cited
UNITED STATES PATENTS
3,631,051  12/1971  Atsumi et al. ............... 260/293.54

*Primary Examiner*—G. Thomas Todd
*Attorney, Agent, or Firm*—Stewart and Kolasch, Ltd.

[57] ABSTRACT

A 3-benzazocine compound of the formula:

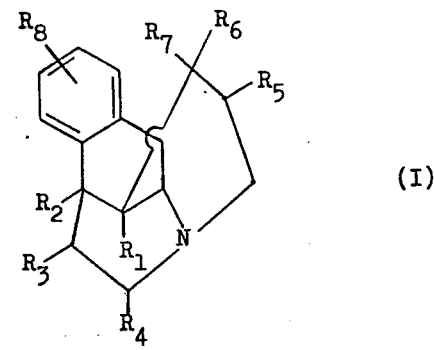

(I)

wherein $R_1$, $R_3$, $R_4$, $R_5$ and $R_8$ are each hydrogen or lower alkyl, $R_2$ is hydrogen, lower alkyl or phenyl and $R_6$ and $R_7$ are each lower alkyl, and its pharmaceutically acceptable acid addition salts, which are useful as analgesics and can be produced by reacting a tetrahydropyridine compound of the formula:

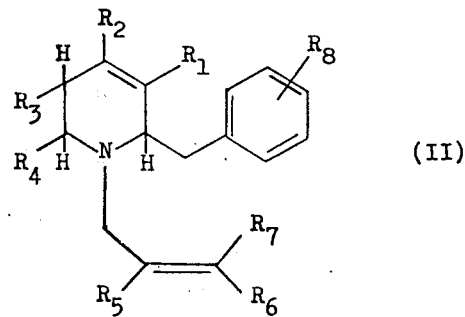

(II)

wherein $R_1$, $R_2$, $R_3$, $R_4$, $R_5$, $R_6$, $R_7$ and $R_8$ are each as defined above or its salt with a Lewis acid.

10 Claims, No Drawings

3-BENZAZOCINE COMPOUNDS

The present invention relates to novel 3-benzazocine compounds and their production and use.

As the result of an extensive study seeking excellent analgesics, it has been found that the following 3-benzazocine compounds exhibit a better analgesic activity than conventional analgesic compounds:

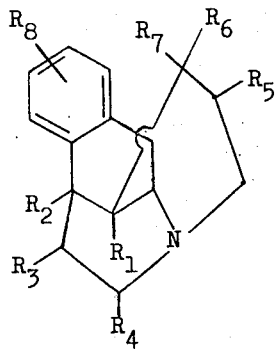

(I)

wherein $R_1$, $R_3$, $R_4$, $R_5$ and $R_8$ are each hydrogen or lower alkyl, $R_2$ is hydrogen, lower alkyl or phenyl and $R_6$ and $R_7$ are each lower alkyl.

The term "lower alkyl" as hereinabove used is intended to mean straight or branched alkyl having 1 to 5 carbon atoms. Specific examples include methyl, ethyl, n-propyl, isopropyl, n-butyl, t-butyl, pentyl, etc.

The chemical structure of the said 3-benzazocine compounds (I) is entirely novel and can be constructed by the application of a unique reaction as heretofore unknown.

Accordingly, a main object of the present invention is to embody the 3-benzazocine compounds (I) which are entirely novel. Another object of this invention is to embody a process for preparing the 3-benzazocine compounds (I) by the utilization of an entirely novel and unique reaction. A further object of the invention is to embody a pharmaceutical composition comprising the 3-benzazocine compounds (I) as active ingredients. These and other objects of the invention are apparent to those skilled in the art from the foregoing and subsequent descriptions.

According to the present invention, the 3-benzazocine compound (I) and its salts can be prepared by reacting a tetrahydropyridine compound of the formula:

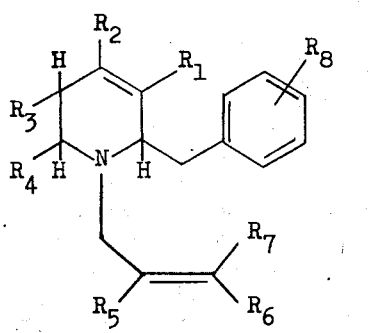

(II)

wherein $R_1$, $R_2$, $R_3$, $R_4$, $R_5$, $R_6$, $R_7$ and $R_8$ are each as defined above or its salt with a Lewis acid, if necessary, followed by treatment with an appropriate acid.

The above reaction proceeds through a pyridine compound of the formula:

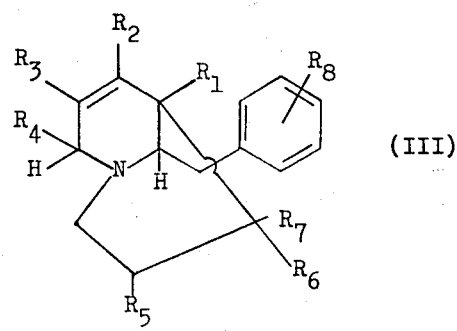

(III)

wherein $R_1$, $R_2$, $R_3$, $R_4$, $R_5$, $R_6$, $R_7$ and $R_8$ are each as defined above, which may be considered to be an intermediate.

The 3-benzazocine compound (I) may be produced directly from the reaction of the tetrahydropyridine compound (II) with a Lewis acid, i.e. without isolating the intermediary pyridine compound (III) in the course of the reaction. When desired, however, the intermediary pyridine compound (III) may be once separated from the reaction mixture and then subjected to further reaction with a Lewis acid to give the 3-benzazocine compound (I).

As the Lewis acid to be employed for ring closure in the process of this invention, there are exemplified hydrobromic acid (e.g. 48% hydrobromic acid), phosphoric acid (e.g. 85% phosphoric acid), phosphoric acid-formic acid, aluminum chloride, aluminum bromide, phosphoric acid-phosphorus pentoxide, etc. The phosphoric acid-phosphorus pentoxide may be obtained by adding phosphorus pentoxide to phosphoric acid and heating the resulting mixture to dissolve it. In this case, the amount of phosphorus pentoxide to phosphoric acid may be such as to obtain an almost anhydrous phosphoric acid as a lower limit and an amount as to maintain fluidity without giving any difficulty to the reaction as an upper limit. For example, when 85% phosphoric acid is employed, the amount of the phosphorus pentoxide is preferably one-half to 2 times the weight of the phosphoric acid.

The amount of the Lewis acid is normally from about one-half to 30 mol, preferably from about 1 to 10 mol per 1 mol of the tetrahydropyridine compound (II). In case of using phosphoric acid-phosphorus pentoxide, the amount is normally from about 1 to 100 times, preferably from about 10 to 50 times, the weight of the tetrahydropyridine compound (II).

When desired, there may be employed any inert organic solvent such as benzene, toluene, hexane or carbon disulfide. The amount of the inert organic solvent may be usually from about 10 to 100 times, favorably from about 5 to 50 times, the weight of the tetrahydropyridine compound (II).

The reaction temperature is ordinarily from about 10° to 200°C. Especially in case of using phosphoric acid-phosphorus pentoxide, the reaction proceeds within a range of about 90° to 200°C, particularly of about 100° to 160°C.

After the reaction is over, the reaction mixture may be subjected to after-treatment by a per se conventional procedure to give a crystalline product. When an oily product is obtained, the reaction mixture may be subjected to distillation under reduced pressure or column chromatography. Such oily product may be treated with a mineral acid or an organic acid which is generally employed to form an acid addition salt and then recrystallized.

The salts of the 3-benzazocine compound (I) include the pharmaceutically acceptable salts prepared, for instance, by the use of an organic acid, an inorganic acid (including an organic acid having an inorganic group) or an organometallic acid. Representative acids for the formation of the pharmaceutically acceptable acid addition salts include formic acid, acetic acid, isobutyric acid, α-mercaptopropionic acid, trifluoroacetic acid, malic acid, fumaric acid, maleic acid, nicotinic acid, cyclamic acid, cytidylic acid, guanylic acid, succinic acid, glutamic acid, tartaric acid, oxalic acid, inosinic acid, pyromucic acid, citric acid, lactic acid, glycolic acid, gluconic acid, saccharinic acid, ascorbic acid, penicillanic acid, benzoic acid, phthalic acid, salicyclic acid, 3,5-dinitrobenzoic acid, cholic acid, 2-pyridinecarboxylic acid, anthranilic acid, 3-hydroxy-2-naphthalic acid, picric acid, quinic acid, tropic acid, 3-indolylacetic acid, barbituric acid, sulfamic acid, methanesulfonic acid, ethanesulfonic acid, isethionic acid, benzenesulfonic acid, p-toluenesulfonic acid, acidic resins, methanephosphoric acid, butylarsonic acid, hydrofluoric acid, hydrochloric acid, hydrobromic acid, hydroiodic acid, perchloric acid, sulfuric acid, phosphoric acid, phosphotungstic acid, molybdic acid, phosphomolybdic acid, etc.

The acid addition salts may be prepared by a per se conventional procedure, for instance, by reacting the 3-benzazocine compound (I) with an acid in water or a suitable organic solvent at a temperature of from about 0°C to room temperature. When the reaction does not proceed smoothly, a little heating is preferable. In the reaction, the 3-benzazocine compound (I) and the acid may be in an equimolar proportion or either reactant may be present in a slight excess amount with respect to the other. In case that the thus prepared acid addition salt is not soluble in the reaction solvent, it can be collected by filtration. When the acid addition salt is soluble, it is obtainable as the residue by removal of the reaction solvent.

The 3-benzazocine compound (I) and its pharmaceutically acceptable acid addition salts may be administered parenterally or orally in any of the usual pharmaceutical forms including tablets, capsules, powders, suspensions, solutions, syrups and the like. Valuable formulations include sustained release preparations which may be compounded by any conventional procedure. Dosage levels vary, generally, depending upon the subject being treated, but range in a daily dosage of from about 1 mg to 50 mg.

Specific examples of the 3-benzazocine compound (I) are as follows:

1,2,3,4,5,6-Hexahydro-6,8,11,12,12-pentamethyl-2,6-methano-3,11-propano-3-benzazocine;
1,2,3,4,5,6-Hexahydro-6,11,12-trimethyl-12-ethyl-2,6-methano-3,11-propano-3-benzazocine;
1,2,3,4,5,6-Hexahydro-6,11,12,12,13-pentamethyl-2,6-methano-3,11-propano-3-benzazocine;
1,2,3,4,5,6-Hexahydro-6,12,12-trimethyl-2,6-methano-3,11-propano-3-benzazocine;
1,2,3,4,5,6-Hexahydro-4,6,12,12-tetramethyl-2,6-methano-3,11-propano-3-benzazocine;
1,2,3,4,5,6-Hexahydro-5,6,11,12,12-pentamethyl-2,6-methano-3,11-propano-3-benzazocine;
1,2,3,4,5,6-Hexahydro-6-phenyl-12,12-dimethyl-2,6-methano-3,11-propano-3-benzazocine, etc.

The novel benzazocine compounds (I) of this invention are all obtained as racemates and each of these racemates can be separated and purified into the optical antipodes by a per se conventional optical resolution procedure: e.g. the racemic bases, dissolved in a suitable inert solvent, are reacted with an optically active acid, and the salts obtained are separated into the diastereoisomers, for example, by reason of their different solubilities, from which the antipodes of the new bases can be liberated by the action of an alkaline agent. The optically active acids generally used are d- and l-α-bromocamphorsulfonic acid, d- and l-tartaric acid, d- and l-benzoyltartaric acid, d- and l-diacetyltartaric acid, d- and l-monomethyl tartrate, d- and l-malic acid, d- and l-mandelic acid, quininic acid, glutamic acid, etc. The individual optical isomers are included in any general structural formulae or nomenclature used herein.

The following Examples are disclosed to illustrate the present invention more precisely but it is not intended to limit the scope of the present invention.

EXAMPLE 1

Phosphorus pentoxide (20 g) was dissolved in 25 g of 85% phosphoric acid by heating, and 1-(3',3'-dimethylallyl)-2-p-methylbenzyl-3,4-dimethyl-1,2,5,6-tetrahydropyridine (3 g) was added thereto under stirring. Thereafter, stirring was continued at 135°–140°C for an additional 20 hours under a nitrogen atmosphere. The reaction mixture was poured into ice-water and made basic with 28% aqueous ammonia under cooling. The resulting mixture was extracted with 150 ml of ether. The ethereal solution was washed with a saturated aqueous solution of sodium chloride, dried over anhydrous sodium sulfate and concentrated to give a yellow oily residue, which was distilled under reduced pressure to give 1,2,3,4,5,6-hexahydro-6,8,11,12,12-pentamethyl-2,6-methano-3,11-propano-3-benzazocine, b.p. 148°–150°C/0.2 mmHg. IR $\nu_{max}^{neat}$ 2800–3000, 1605, 1450, 1400, 1380 $cm^{-1}$.

To a solution of 0.7 g of the free base in 5 ml of acetone, there was added a solution of 0.22 g of oxalic acid in 4 ml of acetone at room temperature, and the resultant mixture was stirred for 1 hour and allowed to stand overnight at 0°C. The precipitate was collected by filtration and washed with acetone. Recrystallization from acetone-methanol (6 : 1) gave 1,2,3,4,5,6-hexahydro-6,8,11,12,12-pentamethyl-2,6-methano-3,11-propano-3-benzazocine oxalate, m.p. 193°–194°C.

EXAMPLE 2

Phosphorus pentoxide (25 g) was dissolved in 30 g of 85% phosphoric acid by heating, and 1-(2',3',3'-trimethylallyl)-2-benzyl-3,4-dimethyl-1,2,5,6-tetrahydropyridine (3.5 g) was added thereto under stirring. Thereafter, stirring was continued at 135°–140°C for an additional 20 hours under a nitrogen atmosphere. The reaction mixture was poured into ice-water and made basic with 28% aqueous ammonia. The resulting mixture was extracted with 200 ml of ether. The ethereal solution was washed with a saturated aqueous solution of sodium chloride, dried over anhydrous sodium sulfate and concentrated to give a yellow oily residue, which was distilled under reduced pressure to give 1,2,3,4,5,6-hexahydro-6,11,12,12,13-pentamethyl-2,6- methano-3,11-propano-3-benzazocine, b.p. 148°–150°C/0.02 mmHg. IR $\nu_{max}^{neat}$ 2800–3000, 1600, 1580, 1460, 1400 cm$^{-1}$.

In the same procedure as in Example 1, there was obtained the oxalate of the free base, m.p. 182°–183°C.

EXAMPLE 3

Phosphorus pentoxide (124 g) was dissolved in 156 g of 85% phosphoric acid by heating, and 1-(3'-methyl-3'-ethylallyl)-2-benzyl-3,4-dimethyl-1,2,5,6-tetrahydropyridine (20 g) was added thereto under stirring. Thereafter, stirring was continued at 135°–140°C for an additional 20 hours under a nitrogen atmosphere. The reaction mixture was poured into ice-water and made basic with 28% aqueous ammonia. The resulting mixture was extracted with 700 ml of ether. The ethereal solution was washed with a saturated aqueous solution of sodium chloride, dried over anhydrous sodium sulfate and concentrated to give a yellow oily residue. Chromatography of the residue (5 g) on 20 g of silica gel, using ethyl acetate as an eluant, gave 1,2,3,4,5,6-hexahydro-6,11,12-trimethyl-12-ethyl-2,6-methano-3,11-propano-3-benzazocine. IR $\nu_{max}^{neat}$ 2800–3000, 1480, 1440, 760, 700 cm$^{-1}$.

In the same procedure as in Example 1, there was obtained the oxalate of the free base, b.p. 174°–176°C.

EXAMPLE 4

Phosphorus pentoxide (197 g) was dissolved in 247 g of 85% phosphoric acid by heating, and 1-(3',3'-dimethylallyl)-2-benzyl-4-methyl-1,2,5,6-tetrahydropyridine (30 g) was added thereto under stirring. Thereafter, stirring was continued at 130° to 140°C for an additional 20 hours under a nitrogen atmosphere. The reaction mixture was poured into ice-water and made basic with 28% aqueous ammonia. The resulting mixture was extracted with 1000 ml of ether. The ethereal solution was washed with a saturated aqueous solution of sodium chloride, dried over anhydrous sodium sulfate and concentrated to give a yellow oily residue. Chromatography of the residue (5 g) on 30 g of silica gel, using ethyl acetate as an eluant, gave 1,2,3,4,5,6-hexahydro-6,12,12-trimethyl-2,6-methano-3,11-propano-3-benzazocine as a white oil. IR $\nu_{max}^{neat}$ 2800–3000, 1500, 1450, 760, 740, 700 cm$^{-1}$.

To a solution of 0.6 g of the free base in 3 ml of acetone there was added a solution of 0.61 g of picric acid in 3 ml of acetone at room temperature, and the resultant mixture was allowed to stand overnight at 0°C. The precipitate was collected by filtration and washed with acetone. Recrystallization from acetone gave the picrate, m.p. 213°–215°C.

EXAMPLE 5

In the same manner as in Example 4 but replacing 1-(3',3'-dimethylallyl)-2-benzyl-4-methyl-1,2,5,6-tetrahydropyridine by an equimolar amount of 1-(3',3'-dimethylallyl)-2-benzyl-4,6-dimethyl-1,2,5,6-tetrahydropyridine, there was prepared 1,2,3,4,5,6-hexahydro-4,6,12,12-tetramethyl-2,6-methano-3,11-propano-3-benzazocine as a colorless oil. IR $\nu_{max}^{neat}$ 2800–3000, 1490, 1420, 760, 740, 720, 700 cm$^{-1}$.

EXAMPLE 6

In the same manner as in Example 4 but replacing 1-(3',3'-dimethylallyl)-2-benzyl-4-methyl-1,2,5,6-tetrahydropyridine by an equimolar amount of 1-(3',3'-dimethylallyl)-2-benzyl-4-phenyl-1,2,5,6-tetrahydropyridine, there was prepared 1,2,3,4,5,6-hexahydro-6-phenyl-12,12-dimethyl-2,6-methano-3,11-propano-3-benzazocine as a brown oil. IR $\nu_{max}^{neat}$ 2800–3000, 1440, 740, 700 cm$^{-1}$.

EXAMPLE 7

A mixture of 4 g of 1-(3'-methyl-3'-n-propylallyl)-2-benzyl-3,4-dimethyl-1,2,5,6-tetrahydropyridine and 50 ml of 47% hydrobromic acid was heated at 130°–140°C for 18 hours. The reaction mixture was made basic with 28% aqueous ammonia and extracted with 150 ml of ether. The ethereal solution was washed with water, dried over anhydrous sodium sulfate and concentrated to a brown oily residue. Chromatography of the residue on 300 g of silica gel, using ethyl acetate as an eluant, gave 1,2,3,4,5,6-hexahydro-6,11,12-trimethyl-12-n-propyl-2,6-methano-3,11-propano-3-benzazocine. IR $\nu_{max}^{neat}$ 2750–3000, 1600–1630, 1450, 800 cm$^{-1}$.

EXAMPLE 8

To a solution of 3 g of 1-(3',3'-dimethylallyl)-2-(p-methylbenzyl)-4-methyl-1,2,5,6-tetrahydropyridine in 15 ml of carbon disulfide, there were added gradually 5 g of aluminum bromide below 20°C, and the resultant mixture was stirred at room temperature for an additional 3 hours. The reaction mixture was poured into 100 ml of ice-water and made basic with 28% aqueous ammonia. The resulting mixture was extracted with 150 ml of ether, washed with water and dried over anhydrous sodium sulfate. The ethereal solution was concentrated to give a yellow oily product. The residue was distilled under reduced pressure to give 1,2,3,4,5,6-hexahydro-6,8,12,12-tetramethyl-2,6-methano-3,11-propano-3-benzazocine, b.p. 135°–138°C/0.13–0.14 mmHg. IR $\nu_{max}^{neat}$ 2800–3000, 1500, 1440, 800, 740, 720 cm$^{-1}$.

EXAMPLE 9

Phosphorus pentoxide (20 g) was dissolved in 25 g of 85% phosphoric acid by heating, and 1-(3',3'-dimethylallyl)-2-benzyl-3,4-dimethyl-1,2,5,6-tetrahydropyridine (3 g) was added thereto under stirring. Thereafter, stirring was continued at 125°–135°C for an additional 20 hours under a nitrogen atmosphere. The reaction mixture was poured into ice-water and made basic with 28% aqueous ammonia. The resulting mixture was extracted with 150 ml of ether. The ethereal solution was washed with a saturated aqueous solution of sodium chloride, dried over anhydrous sodium sulfate and concentrated to give a yellow oily residue, which was distilled under reduced pressure to give 1,2,3,4,5,6-hexahydro-6,11,12,12-tetramethyl-2,6-methano-3,11-propano-3-benzazocine, b.p. 117°–125°C/0.06 mmHg. IR $\nu_{max}^{neat}$ 1490, 760, 715, 695 cm$^{-1}$.

The free base was converted to the hydrochloride by contacting with gaseous hydrogen chloride. The precipitate was collected by filtration and washed with ether. Recrystallization from acetone-methanol gave the hydrochloride of the free base, m.p. 240°–240.5°C.

The starting tetrahydropyridine compounds (II) are generally known and can be produced by the processes as described in J. Org. Chem., 19, 1432 (1954); ibid., 24, 1435 (1959); ibid., 27, 245 (1962); ibid., 27, 2144 (1962); ibid., 28, 2470 (1963) and J. Med. Chem., 7, 410 (1964); ibid., 8, 563 (1965); ibid., 8, 694 (1965), or any processes similar thereto.

What is claimed is:

1. A 3-benzazocine compound of the formula:

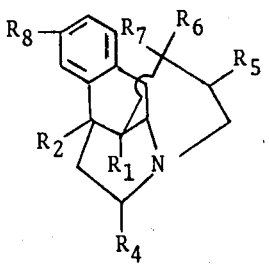

wherein $R_1$, $R_4$, $R_5$ and $R_8$ are each hydrogen or lower alkyl, $R_2$ is hydrogen, lower alkyl or phenyl and $R_6$ and $R_7$ are each lower alkyl, and pharmaceutically acceptable salts thereof.

2. 1,2,3,4,5,6-Hexahydro-6,8,11,12,12-pentamethyl-2,6-methano-3,11-propano-3-benzazocine and the oxalate thereof.

3. 1,2,3,4,5,6-Hexahydro-6,11,12,12,13-pentamethyl-2,6-methano-3,11-propano-3-benzazocine and the oxalate thereof.

4. 1,2,3,4,5,6-Hexahydro-6,11,12-trimethyl-12-ethyl-2,6-methano-3,11-propano-3-benzazocine and the oxalate thereof.

5. 1,2,3,4,5,6-Hexahydro-6,12,12-trimethyl-2,6-methano-3,11-propano-3-benzazocine and the picrate thereof.

6. 1,2,3,4,5,6-Hexahydro-4,6,12,12-tetramethyl-2,6-methano-3,11-propano-3-benzazocine.

7. 1,2,3,4,5,6-Hexahydro-6-phenyl-12,12-dimethyl-2,6-methano-3,11-propano-3-benzazocine.

8. 1,2,3,4,5,6-Hexahydro-6,11,12-trimethyl-12-n-propyl-2,6-methano-3,11-propano-3-benzazocine.

9. 1,2,3,4,5,6-Hexahydro-6,8,12,12-tetramethyl-2,6-methano-3,11-propano-3-benzazocine.

10. 1,2,3,4,5,6-Hexahydro-6,11,12,12-tetramethyl-2,6-methano-3,11-propano-3-benzazocine and the hydrochloride thereof.

* * * * *